(12) United States Patent
Kleinschmidt et al.

(10) Patent No.: US 6,547,773 B2
(45) Date of Patent: Apr. 15, 2003

(54) DISPOSABLE DIAPER HAVING INTEGRAL CUFFS AND SIDE PANELS

(75) Inventors: David C. Kleinschmidt, Fairfield, OH (US); Karen M. Davis, Cincinnati, OH (US); Terrill A. Young, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/871,719

(22) Filed: Jun. 1, 2001

(65) Prior Publication Data

US 2002/0183713 A1 Dec. 5, 2002

(51) Int. Cl.[7] .................................................. A61F 13/15
(52) U.S. Cl. ........................... 604/385.101; 604/385.28
(58) Field of Search ...................... 604/385.24–385.29, 604/385.101, 385.04

(56) References Cited

U.S. PATENT DOCUMENTS

| | | | |
|---|---|---|---|
| 4,695,278 A | | 9/1987 | Lawson |
| 5,254,111 A | | 10/1993 | Cancio et al. |
| 5,451,442 A | * | 9/1995 | Pieniak et al. ............... 428/167 |
| 5,628,737 A | * | 5/1997 | Dobrin et al. ............... 604/383 |
| 5,643,243 A | | 7/1997 | Klemp |
| 5,672,166 A | * | 9/1997 | Vandemoortele ............... 156/164 |
| 5,746,732 A | * | 5/1998 | Olsson et al. ........... 604/385.28 |
| 5,776,121 A | | 7/1998 | Roe et al. |
| 5,947,949 A | | 9/1999 | Inoue et al. |
| 6,056,733 A | * | 5/2000 | Kielpikowski ......... 604/385.04 |
| 6,123,694 A | | 9/2000 | Pieniak et al. |
| 6,174,302 B1 | | 1/2001 | Kumasaka |
| 6,183,459 B1 | | 2/2001 | Yamamoto et al. |
| 6,328,722 B1 | * | 12/2001 | Lavash et al. ......... 604/385.04 |

* cited by examiner

Primary Examiner—Dennis Ruhl
Assistant Examiner—C Lynne Anderson
(74) Attorney, Agent, or Firm—Michael S. Kolodesh; Jay A. Krebs; Ken K. Patel

(57) ABSTRACT

A disposable absorbent article having a pair of barrier leg cuffs and a pair of side panels is provided. The barrier leg cuffs are disposed along opposing sides of an absorbent core and the side panels are disposed outboard of the barrier leg cuffs along opposing sides of the absorbent article. The barrier leg cuffs are integrally formed with the side panels from a single nonwoven ply.

14 Claims, 3 Drawing Sheets

DISPOSABLE DIAPER HAVING INTEGRAL CUFFS AND SIDE PANELS

FIELD OF THE INVENTION

This invention is directed to hygienic absorbent articles, such as diapers, training pants and the like. Particularly, the invention is directed to a disposable diaper including cuffs that are integral with the side panels.

BACKGROUND OF THE INVENTION

Infants and other incontinence individuals wear disposable absorbent articles such as diapers to receive and contain urine and other body exudates. Absorbent articles function both to contain and to isolate the discharged materials from the body of the wearer and from the wearer's garments and bed clothing. Disposable absorbent articles having many different basic designs are known in the art. Contemporary disposable diapers comprise a fluid pervious topsheet, a fluid impervious backsheet, an absorbent core, and elasticized leg flaps. Each of the elasticized leg flaps are generally formed from an elastic member disposed along longitudinal edges of the absorbent core and enclosed between the topsheet and the backsheet. These elasticized leg flaps generally prevent wicking and overflow from the fluid laden diaper to clothing contacting the edges of the diaper. In addition, the elasticized leg flaps provide a gasketing action about the legs of the wearer to maintain a seal about the leg and to minimize gapping. However, leakage along the perimeter of the diaper may still occur. For instance, as the diaper is worn for long periods of time, forces tend to act on the diaper to degrade the initial fit on the wearer causing large gaps and sagging particularly around the legs and waist. Thus, as liquids are deposited onto the topsheet, some of the liquid is not immediately absorbed through the topsheet and migrates toward the edges of the diaper where it can leak through or past the gaps in the diaper and come in contact with clothing or undergarments where it can be absorbed by and wicked into such garments.

Disposable diapers have been provided with separately attached barrier cuffs that inhibit loose fecal material or gushes of urine or liquids from soiling the wearer's clothing. The barrier cuffs restrain the free flow of this material and provide a structure to hold such material within the diaper. Typically, the barrier cuffs are formed by attaching an independent web of cuff material to the topsheet web or to the topsheet of a completed chassis. For example, commonly assigned U.S. Pat. No. 4,695,278 to Lawson teaches a dual cuff arrangement in which the barrier cuff is a separate element joined to the topsheet. The addition of the independent web or cuff material to the topsheet increases the bulk of the chassis and may result in a product that is noisy in use. What's more, when the barrier cuff is attached to the topsheet as a separate element, special machinery dedicated to attaching the barrier cuffs is required, which adds to the cost of the completed article.

Furthermore, when conventional diapers are manufactured, notches are cut in the sides of the article to provide a contour for the legs of the person who will wear the article. For example, leg notches account for approximately 15–20% of the area of an absorbent article. The portion removed from the article to create the leg notches has no further use in the manufacturing process and is discarded. Thus, the current methods of manufacturing diapers produce a large volume of unnecessary waste.

Thus, it would be desirable to provide a disposable absorbent article, such as a diaper, having good containment characteristics and comfortable to the wearer. It would also be desirable to provide a disposable absorbent article having good containment and breathability characteristics that is economical and easy to manufacture at high speeds.

SUMMARY OF THE INVENTION

In order to solve one or more of the problems found in the art, a disposable absorbent article is provided comprising a liquid pervious topsheet having a body-facing surface, a liquid impervious backsheet forming the longitudinal edges of the absorbent article, and an absorbent core disposed between the topsheet and the backsheet. Barrier leg cuffs are disposed along opposing sides of the absorbent core and a pair of side panels are disposed outboard of the barrier leg cuffs on opposing sides of the article. Center portions of the side panels are congruent with the longitudinal edges of the absorbent article while end portions extend beyond the longitudinal edges forming front and rear ear panels.

The barrier leg cuffs and the side panels are integrally formed from a single nonwoven ply. The single nonwoven ply may be profiled to provide a nonwoven material having different basis weight regions. For instance, the single nonwoven ply may comprise a first region forming the barrier leg cuffs and a second region forming the side panels wherein the first region has a lower basis weight than the second region. The profiled configuration can provide a side panel delivering the material strength needed for securing a fastening device to the diaper while providing coverage of the wearer's skin that is not only breathable and quiet, but also aesthetically pleasing. At the same time the barrier leg cuff region can be provided at a lower basis weight to deliver a softness that is comfortable to the wearer's skin.

In an alternate embodiment, the topsheet, barrier leg cuffs, and the side panels are formed from a single nonwoven ply. For this embodiment, the single nonwoven ply may comprise a third region forming the topsheet. The third region may have a different basis weight than the first and second regions and include a hydrophilic coating.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
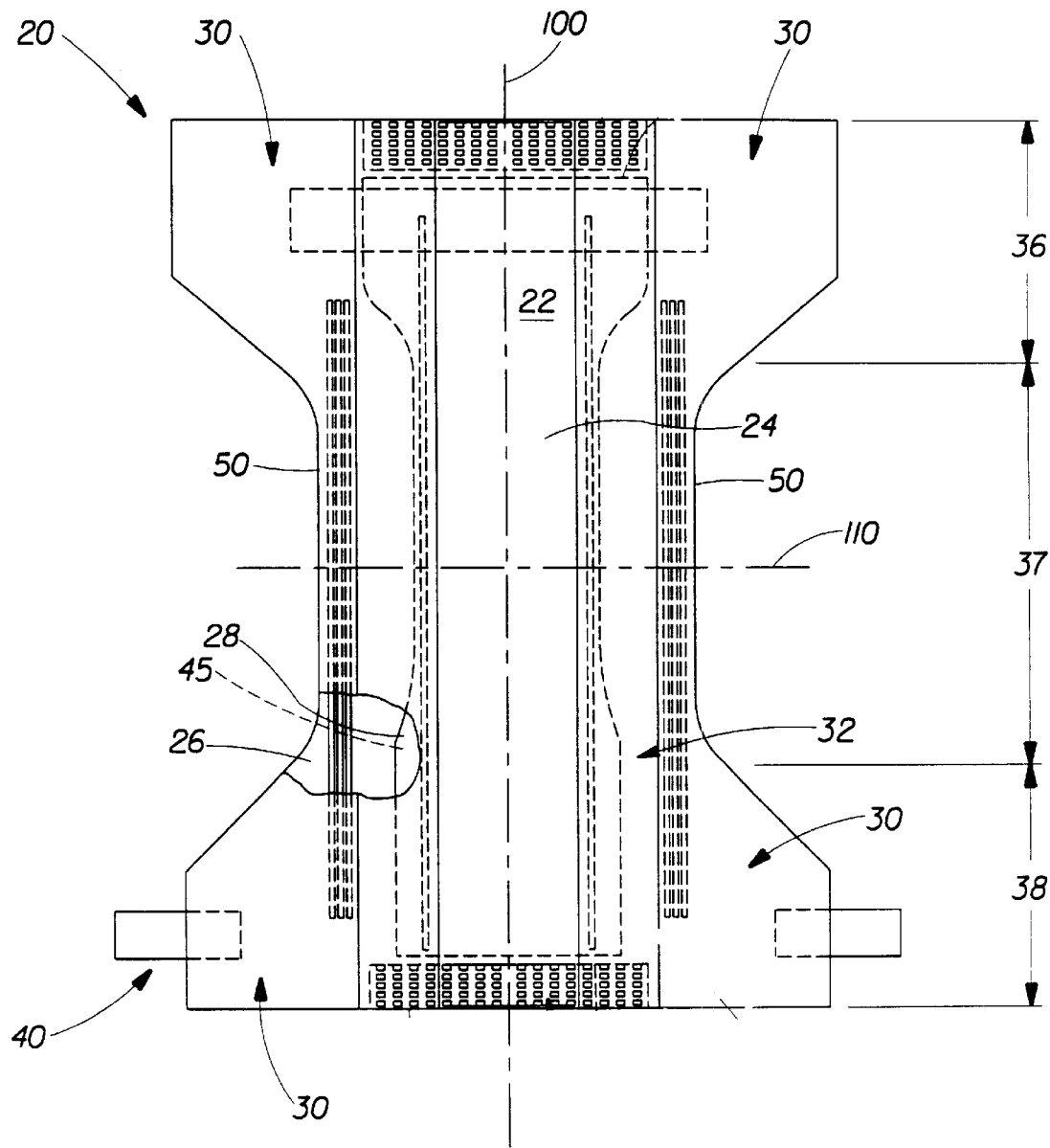
FIG. 1 is a plan view of a disposable diaper.

While this specification concludes with claims particularly pointing out and distinctly claiming that which is regarded as the invention, it is anticipated that the invention can be more readily understood through reading the following detailed description of the invention and study of the included drawings.

DEFINITIONS

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The "x-y plane refers to the plane congruent with the longitudinal and transverse directions.

Basis weight is the weight (in grams) per unit area (in square meters) of a sample reported in grams per square meter.

Machine direction, designated MD, is the direction parallel to the flow of web material through the product manufacturing equipment.

Cross machine direction, designated CD, is the direction perpendicular to the machine direction in the same plane of web material.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s), which in turn are affixed to the other element.

A "unitary" absorbent article refers to absorbent articles, which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "barrier hydrohead" refers to a materials ability to support a volume of water when its hydrohead is measured in accordance with Method 5514—Federal Test Methods Standard No. 191A.

The present invention provides a disposable absorbent article including a pair of barrier cuffs disposed along opposing sides of a longitudinal axis and a pair of side panels disposed outboard of the barrier cuffs. The barrier cuffs are integrally formed with the side panels from a single ply of nonwoven. The integral cuff/side panel design is equally applicable to disposable absorbent articles including disposable diapers, training pants, incontinence briefs, incontinence undergarments, absorbent inserts, diaper holders and liners, feminine hygiene garments, and the like. One embodiment of a disposable absorbent article of the present invention is a unitary disposable absorbent article, such as the disposable diaper 20, shown in FIG. 1.

FIG. 1 is a plan view of the diaper 20 in its flat out, uncontracted state (i.e., without elastic induced contraction) with portions of the structure being cut away to more clearly show the underlying structure of the diaper 20 and with the portion of the diaper 20 which contacts the wearer facing the viewer. The diaper 20 includes a longitudinal axis 100 and a transverse axis 110. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions, 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The chassis 22 of the diaper 20 comprises the main body of the diaper 20. The chassis 22 comprises an outer covering including a liquid pervious topsheet 24 and/or a liquid impervious backsheet 26 and at least a portion of an absorbent core 28 encased between the topsheet 24 and the backsheet 26. For unitary absorbent articles, the chassis 22 comprises the main structure of the diaper with other features added to form the composite diaper structure. While the topsheet 24, the backsheet 26, and the absorbent core 26 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The topsheet 24 may be fully or partially elasticized or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets", each of which is incorporated by reference herein.

The backsheet 26 is generally that portion of the diaper 20 positioned adjacent garment facing surface 45 of the absorbent core 28 which prevents the exudates absorbed and contained therein from soiling articles which may contact the diaper 20, such as bed sheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials, which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

Figure 2:
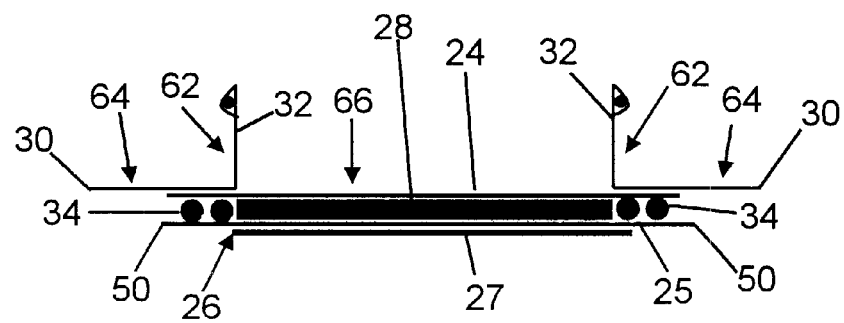
FIG. 2 is a cross sectional view of a diaper having barrier leg cuffs and side panels integrally formed from a single nonwoven ply.
Figure 3:
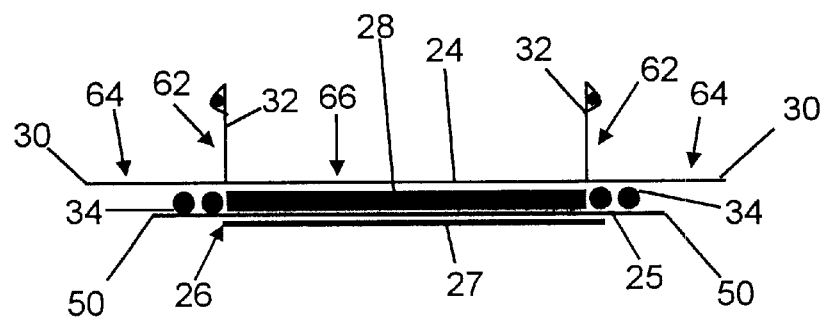
FIG. 3 is a cross sectional view of a diaper having a topsheet, barrier leg cuffs, and side panels integrally formed from a single nonwoven ply.

Further, as shown in FIGS. 2 and 3, the backsheet 26 may comprise a cloth-like backsheet including a microporous film 25 having a garment-facing surface covered by a nonwoven 27. The nonwoven 27 may be bonded to the microporous film via adhesive, ultrasonic, or infrared bonds. The bonding of the nonwoven to the film adds stiffness, which may inhibit the extensibility of the backsheet 26. Consequently, the nonwoven is preferably limited to a center portion of the film backsheet, leaving portions along the longitudinal edges 50 exposed.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, infrared bonds, or any other suitable attachment means or combinations of these attachment means as are known in the art.

The diaper 20 preferably further includes leg cuffs 32 which provide improved containment of liquids and other body exudates. Leg cuffs 32 may also be referred to as leg bands, side flaps, barrier cuffs, or elastic cuffs. U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs), which improve the containment of the leg regions and are incorporated herein by reference.

The barrier leg cuffs 32 may include a base end attached to the topsheet in the x-y plane and a free end extending from the topsheet in the z direction to a free end which is folded over to enclose one or more elastic strands. Alternatively, the barrier leg cuffs 32 may include flipped inner cuffs made from a single nonwoven material, which is folded over to form a free end. Elastic elements may be disposed in the cuffs, one at the fold forming the free end and another intermediate the fold forming the free end and an opposite end forming the base of the cuff. In either embodiment, longitudinal inner sides of the barrier leg cuffs 32 may be attached to the topsheet 24 of the product while longitudinal outer sides are folded back outwards with the longitudinally opposite ends attached to the first waist region 36 and the second waist region 38 of the of the chassis 22.

The disposable diaper may also include a pair of elastically contractible gasketing leg cuffs 34. The gasketing leg cuffs 34 are generally disposed outside of the barrier leg cuffs 32 adjacent to the longitudinal edges 50 of the backsheet and comprise at least one, preferably more than one elastic strand interposed and secured between the backsheet and the topsheet. U.S. Pat. No. 3,860,003 describes a disposable diaper which provides a contractible leg opening having a side flap and one or more elastic members to provide an elasticized leg cuff (a gasketing cuff) and is incorporated herein by reference. Further, U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs and are also incorporated herein by reference.

The diaper 20 also comprises side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the caregiver pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S.

Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151, 092 issued to Buell on Sep. 9, 1992; U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit", and U.S. Pat. No. 6,004,306 entitled "Absorbent Article With Multi-Directional Extensible Side Panels" issued to Robles et al. on Dec. 21, 1999; each of which is incorporated herein by reference.

The diaper 20 may also include a fastening system 40. The fastening system 40 may be attached to the side panels 30 to preferably maintain the first waist region 36 and the second waist region 38 in a configuration so as to provide lateral tensions about the circumference of the diaper 20 to hold the diaper 20 on the wearer. The fastening system 40 preferably comprises a surface fastener such as tape tabs, hook and loop fastening components and/or hermaphroditic fastening components, although any other known fastening means are generally acceptable. In order to provide a sustained fit about the wearer, the fasteners of the present invention may be elastically extensible or stretchable or may be attached to the side panels via a tab that is elastically extensible or stretchable.

Some exemplary surface fastening systems are disclosed in U.S. Pat. No. 3,848,594 entitled "Tape Fastening System for Disposable Diaper" issued to Buell on Nov. 19, 1974; U.S. Pat. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. application Ser. No. 09/143,184 entitled "Absorbent Article Fastening Device" in the names of Kline et al. filed on Aug. 8, 1998. The fastening system 40 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987 to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997.

An embodiment illustrated in FIG. 2 shows a pair of barrier leg cuffs 32 disposed on opposing sides of the longitudinal axis 100 of the diaper 20 along with a pair of side panels 30, disposed outboard of the barrier leg cuffs 32, integrally formed such that a combination of one barrier leg cuff 32 and one side panel 30 is made from a single nonwoven ply. These single nonwoven plies may be attached to the chassis 22 using adhesives, ultrasonic bonds, radio frequency bonds, or other suitable means. Since side panels 30 are generally made from two or more plies, the single nonwoven ply design reduces the amount of material required resulting in a savings in material costs as well as a product design that is less bulking and potentially lighter in weight.

In order to meet the functional needs of the components, the combination barrier leg cuff 32 and side panel 30 may be integrally formed from a single nonwoven ply of material providing the containment capability and softness of a cuff while at the same time providing the tensile strength capable of securing a fastener to the side panel. The material properties necessary to provide these attributes are somewhat conflicting since a material having the strength desired for the side panel 30 generally exhibits a stiffness that is incapable of providing the desired softness for the barrier leg cuff 32. The single nonwoven ply may comprise a profiled nonwoven including a first region 62 offering the softness and containment properties desirable for the barrier cuffs 32 and a second region 64 having a tensile strength desirable for the side panels 30.

For instance, a polypropylene spunbond thermal point bonded nonwoven, which is profiled in spunlaid filaments, may be provided. The profiled filaments can be made to form a low basis weight region for the first region 62 providing adequate barrier for containment and softness for comfort and a high basis weight region for the second region 64 providing the tensile strength necessary for fastening. For the present invention, the basis weight of the second region 64 is 100% of the basis weight of the first region 62, preferably, 125% of the basis weight of the first region 62 and most preferably, 150% of the basis weight of the first region 62. Basis weight is measured using industry standards ASTM D3776-96.

In an alternate embodiment shown in FIG. 3, the liquid pervious topsheet 24, the pair of barrier leg cuffs 32 and the pair of side panels 30 are integrally formed from a single nonwoven ply. For this embodiment the profiled configuration of the single nonwoven ply comprises a third region 66 forming the permeable topsheet 24. The third region 66 forming the topsheet 24 may have a basis weight that is less than the basis weight of the second region 64 and/or less than or equal to the basis weight of the first region. For this embodiment, the third region 66 may be treated with a hydrophilic coating to enhance the hydrophilicity.

For each embodiment previously described, the profiled configuration may provide a second region 64 having a higher CD tensile strength than the first and third regions 62, 66 as well as a higher opacity than the first and third regions 62, 66. The CD tensile strength of the first region 62 may range from about 5.5 N/cm to about 12.0 N/cm, preferably from about 7.0 N/cm to about 10.0 N/cm. CD tensile strength is measured using industry standards ASTM D5035-95 (modified to 2 inch gage length and 5 inches/minute extension rate). The opacity of the second region 64 ranges from about 35 to about 55 units, preferably from about 45 units to about 55 units where opacity is measured using industry standards INDA IST 60.1-95.

Further, the primarily function of the barrier leg cuffs 32 is to inhibit loose fecal material or gushes of urine or liquids from soiling the wearer's clothing, therefore, the first region 62 of the single nonwoven ply forming the cuff 32 should provide a level of containment. The level of containment may be measured by barrier hydrohead (previously defined) using industry standards (Rising Column Strike Through)—AATCC 127-1985. The first region 62 has a barrier hydrohead greater than about 60 mm of water, preferably greater than about 100 mm of water. Since the first region 62 has a lower basis weight than the second region 64, the barrier hydrohead of the second region 64 is greater than that of the first region 62.

Devices for producing spunbond thermal point bonded nonwoven from extruded polymers are well known in the art. Extruded polymers under pressure are forced through a spinneret forming a vertically oriented curtain of downward advancing filaments. The spinneret comprises an assembly, which is known in the art, and includes a plurality of nozzle bores with hole diameters customary for filament production. The spinneret assembly can be adapted to the fluidity of the melt so that every nozzle bore has the same rate of flow.

Upon exiting the spinneret, the filaments are quenched with air in conjunction with a suction-type drawing or attenuating air slot or other devices. U.S. Pat. No. 5,292,239 issued to Zeldin, et al., Mar. 8, 1994, discloses a device that reduces significant turbulence in the airflow in order to uniformly and consistently apply a drawing force to the filaments. The drawing unit comprises an open upper end, an open lower end, and an air supply manifold supplying compressed air to internal nozzles oriented in a downward direction. As compressed air flows through the internal nozzles, air is drawn into the open upper end of the drawing unit forming a rapidly moving stream of air flowing in the downward direction. The air stream produces a drawing force on the filaments causing them to be attenuated or stretched before exiting the open lower end of the drawing unit.

Upon exiting the drawing unit, the filaments are deposited on a moving conveyor belt to form a web comprising filaments. The filaments are then joined to each other through conventional techniques such as thermal point bonding. A preferred process for producing nonwoven plies of the present invention is described in U.S. Pat. No. 5,688,468 issued to Lu, Nov. 18, 1997, which is incorporated herein by reference.

For the present invention, the profiled single nonwoven ply may be spunbonded in a variety of different ways, preferably profiled in the cross machine direction of the material. For instance, preformed strips of nonwoven may be laid down on a driven belt in the machine direction and spaced apart in the cross machine direction. A uniform layer of spunbonded filaments may be drawn and deposited on top of the nonwoven strips forming the profiled configurations. As a result, the areas including the nonwoven strips form the second (high basis weight) regions 64 while the spaces therebetween form the first (low basis weight) regions 62. Conversely, a uniform preformed nonwoven web may be laid on the belt and additional spunbonded nonwoven may be drawn in strips and deposited onto the uniform preformed web.

Alternatively, the profiled single nonwoven may be produced using a profiled drawing device to draw a higher density of filaments in one area of the web and a lower density of filaments in other areas of the web. The higher density of filaments results in a higher basis weight region than the lower density of filaments. For this embodiment, a dual drawing device can be made to take a uniform extrusion of filaments from the spinneret and lay down more filaments in high-density areas and less filaments in low density areas, preferably in certain areas across the web.

In another embodiment, the profiled single nonwoven may be made by deflecting filaments into high and low density areas across the web during or after the drawing process. The deflection can be induced using guided air during the drawing process or by a mechanical means such as a plow device. In either case, a profiled web is produced preferably across the web by creating a sparse lay down of filaments in low-density areas across the web and a heavy lay down of filaments in high-density areas.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable absorbent article having a longitudinal axis, a first waist region, a second waist region, and a crotch region interposed therebetween, the disposable absorbent article comprising:

a liquid pervious topsheet;

a liquid impervious backsheet having opposing longitudinal edges;

an absorbent core disposed between the topsheet and the backsheet;

a pair of barrier leg cuffs disposed along opposing sides of the longitudinal axis; and a pair of side panels disposed outboard of the barrier leg cuffs, each of the side panels having a center portion coterminous with a longitudinal edge of the backsheet in the crotch region and two opposing end portions extending transversely outboard of the longitudinal edge in the first waist region and the second waist region;

wherein the barrier leg cuffs are integrally formed with the side panels from single nonwoven plies, wherein each of the single nonwoven plies comprises a first region forming the barrier leg cuff and a second region forming the side panel wherein the first region has a lower basis weight than the second region.

2. The disposable absorbent article according to claim 1 wherein the basis weight of the second region is at least 150% of the basis weight of the first region.

3. The disposable absorbent article according to claim 1 wherein the second region has a CD tensile strength ranging from about 5.5 N/cm to about 12.0 N/cm.

4. The disposable absorbent article according to claim 1 wherein the first region has an average barrier hydrohead of about 100 mm water.

5. The disposable absorbent article according to claim 1 wherein the second region has higher opacity than the first region.

6. The disposable absorbent article according to claim 5 wherein the second region has an opacity ranging from about 35 to about 55 units.

7. A disposable absorbent article having a longitudinal axis, a first waist region, a second waist region, and a crotch region interposed therebetween, the disposable absorbent article comprising:

a liquid pervious topsheet;

a liquid impervious backsheet having opposing longitudinal edges;

an absorbent core disposed between the topsheet and the backsheet;

a pair of barrier leg cuffs disposed along opposing sides of the longitudinal axis; and a pair of side panels disposed outboard of the barrier leg cuffs, each of the side panels having a center portion coterminous with a longitudinal edge of the backsheet in the crotch region and two opposing end portions extending transversely outboard of the longitudinal edge in the first waist region and the second waist region;

wherein the liquid pervious topsheet, the barrier leg cuffs and the side panels are integrally formed from a single nonwoven ply, wherein the single nonwoven ply comprises a first region forming the barrier leg cuffs, a second region forming the side panels and a third region forming the topsheet wherein the first region and the third region have lower basis weights than the second region.

8. The disposable absorbent article according to claim 7 wherein the basis weight of the second region is at least 150% of the basis weight of the first region.

9. The disposable absorbent article according to claim 7 wherein the second region has a CD tensile strength ranging from about 5.5 N/cm to about 12.0 N/cm.

10. The disposable absorbent article according to claim 7 wherein the third region includes a hydrophilic coating.

11. A disposable diaper having a longitudinal axis, a first waist region, a second waist region, and a crotch region interposed therebetween, the disposable diaper comprising:

a liquid pervious topsheet;

a liquid impervious backsheet having opposing longitudinal edges;

an absorbent core disposed between the topsheet and the backsheet; and two single nonwoven plies disposed along opposing sides of the longitudinal axis, each of the single nonwoven plies comprising a first region and a second region wherein the second region has a higher basis weight than the first region, and wherein the first region forms a barrier leg cuff and the second region forms a side panel disposed outboard of the barrier leg cuff, each of the side panels having a center portion coterminous with a longitudinal edge of the backsheet in the crotch region and two opposing end portions extending transversely outboard of the longitudinal edge in the first waist region and the second waist region.

12. The disposable absorbent article according to claim 11 wherein the backsheet comprises a microporous breathable film and wherein a center portion of the microporous breathable film is covered by a nonwoven layer on a garment-facing surface of the backsheet leaving portions along the longitudinal edges exposed to enhance the elasticity of the article and provide an improved sustained fit.

13. The disposable diaper according to claim 11 wherein the basis weight of the second region is at least 150% of the basis weight of the first region.

14. The disposable diaper according to claim 11 wherein the second region has a CD tensile strength ranging from about 5.5 N/cm to about 12.0 N/cm.

* * * * *